United States Patent
Krill et al.

(10) Patent No.: US 9,580,374 B2
(45) Date of Patent: Feb. 28, 2017

(54) METHOD FOR PRODUCING METHACROLEIN AND THE CONDITIONING/DRAINING THEREOF FOR DIRECT OXIDATIVE ESTERIFICATION

(71) Applicants: Steffen Krill, Muehltal (DE); Matthias Groemping, Darmstadt (DE); Alexander Lygin, Griesheim (DE); Torsten Balduf, Pfungstadt (DE); Rudolf Burghardt, Darmstadt (DE)

(72) Inventors: Steffen Krill, Muehltal (DE); Matthias Groemping, Darmstadt (DE); Alexander Lygin, Griesheim (DE); Torsten Balduf, Pfungstadt (DE); Rudolf Burghardt, Darmstadt (DE)

(73) Assignee: EVONIK ROEHM GmbH, Darmstadt (DE)

(*) Notice: Subject to any disclaimer, the term of this patent is extended or adjusted under 35 U.S.C. 154(b) by 0 days.

(21) Appl. No.: 14/916,440

(22) PCT Filed: Aug. 27, 2014

(86) PCT No.: PCT/EP2014/068171
§ 371 (c)(1),
(2) Date: Mar. 3, 2016

(87) PCT Pub. No.: WO2015/043861
PCT Pub. Date: Apr. 2, 2015

(65) Prior Publication Data
US 2016/0200660 A1    Jul. 14, 2016

(30) Foreign Application Priority Data
Sep. 26, 2013   (EP) .................... 13186137

(51) Int. Cl.
| | | |
|---|---|---|
| C07C 45/75 | (2006.01) |
| C07C 45/80 | (2006.01) |
| C07C 45/82 | (2006.01) |
| C07C 67/54 | (2006.01) |
| C07C 67/39 | (2006.01) |
| C07C 45/84 | (2006.01) |

(52) U.S. Cl.
CPC ............ *C07C 45/75* (2013.01); *C07C 45/80* (2013.01); *C07C 45/82* (2013.01); *C07C 45/84* (2013.01); *C07C 67/39* (2013.01); *C07C 67/54* (2013.01)

(58) Field of Classification Search
None
See application file for complete search history.

(56) References Cited

U.S. PATENT DOCUMENTS

| | | |
|---|---|---|
| 4,496,770 A | 1/1985 | Duembgen et al. |
| 4,638,085 A | 1/1987 | Broecker et al. |
| 5,969,178 A | 10/1999 | Okamoto et al. |
| 2014/0206831 A1 | 7/2014 | Venkitasubramanian |

FOREIGN PATENT DOCUMENTS

| | | |
|---|---|---|
| CN | 1817844 A | 8/2006 |
| CN | 101074192 A | 11/2007 |
| WO | 2012/154450 A2 | 11/2012 |

OTHER PUBLICATIONS

Dimitratos et al. Chem. Sci., 2012, 3, 20-44.*
U.S. Appl. No. 15/037,171, filed May 17, 2016, Burghardt, et al.
U.S. Appl. No. 15/030,775, filed Apr. 20, 2016, Krill, et al.
International Search Report Issued Oct. 28, 2014, in PCT/EP2014/068171 Filed Aug. 27, 2014.
European Search Report Issued Feb. 21, 2014, in EP 13 18 6137.9 Filed Sep. 26, 2013.

* cited by examiner

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

The present invention relates to a process for preparing methyl methacrylate by direct oxidative esterification of methacrolein and the preparation of methacrolein. It is a feature of this novel process that it was possible to distinctly increase the yield and the efficiency of the process compared to the prior art through a sequence of different distillation steps.

16 Claims, 2 Drawing Sheets

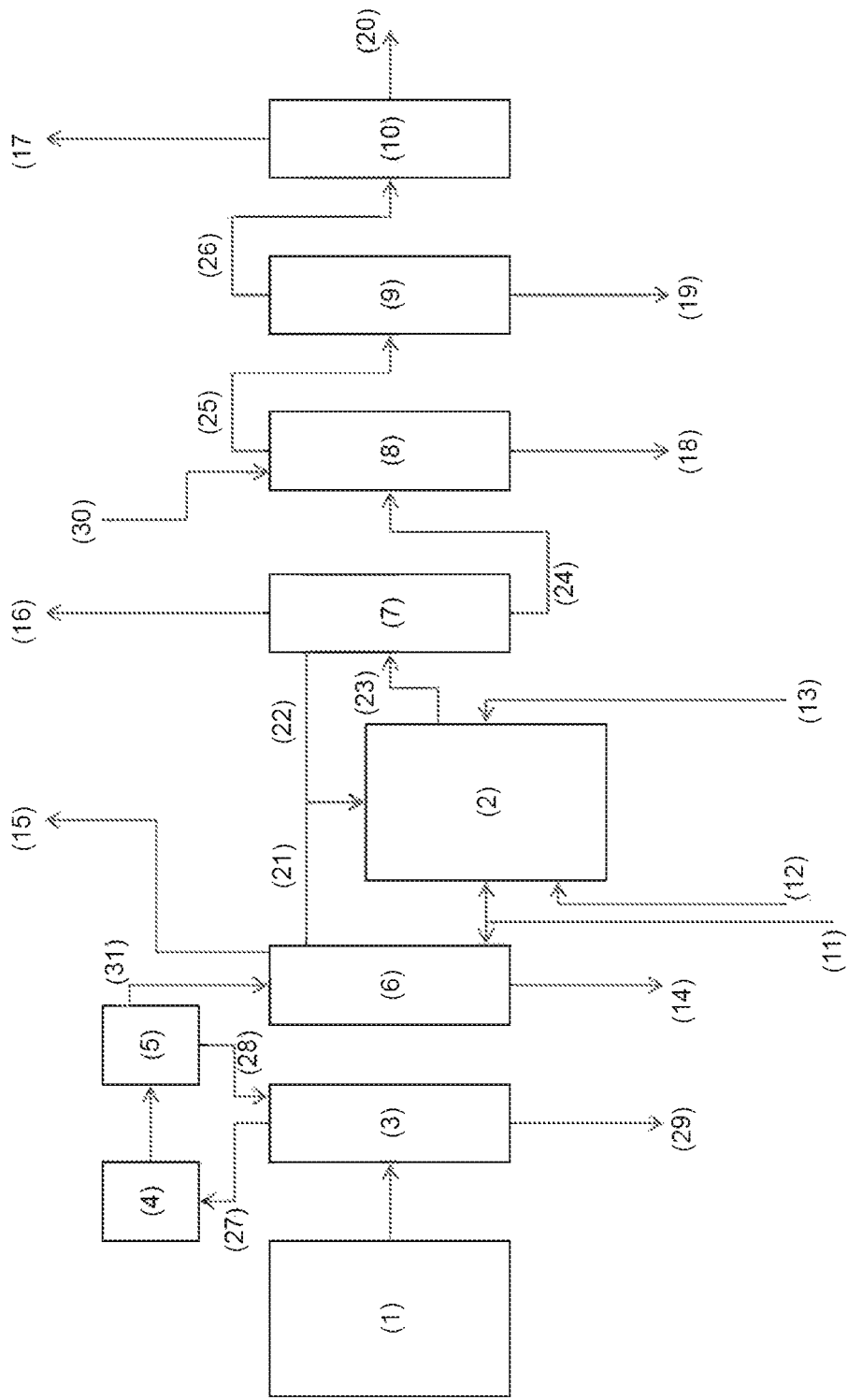
Fig. 1: Schematic process flow diagram

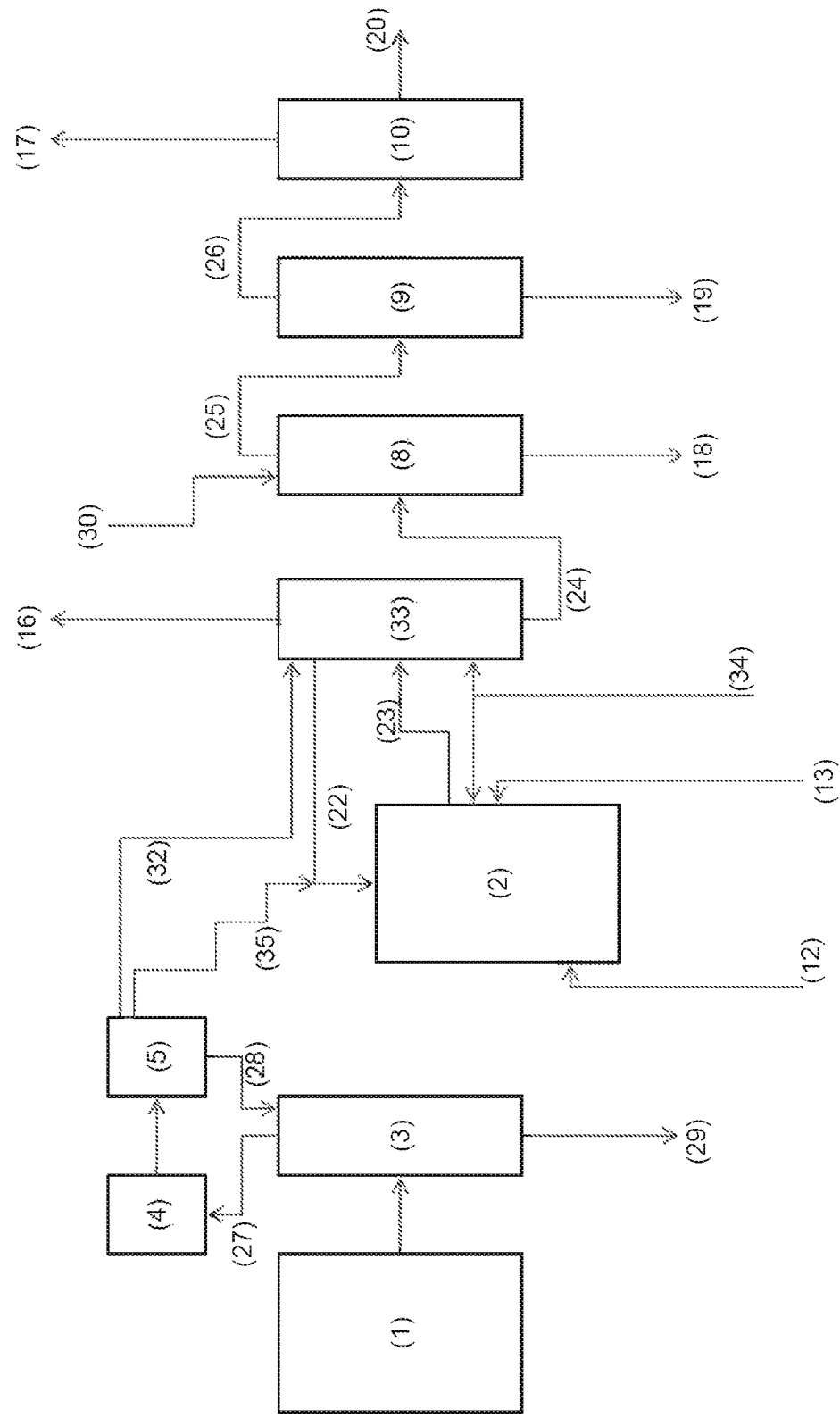
Fig. 2: Schematic process flow diagram

METHOD FOR PRODUCING METHACROLEIN AND THE CONDITIONING/DRAINING THEREOF FOR DIRECT OXIDATIVE ESTERIFICATION

FIELD OF THE INVENTION

The present invention relates to a process for preparing methyl methacrylate by direct oxidative esterification of methacrolein and the preparation of methacrolein. It is a feature of this novel process that it was possible to distinctly increase the yield and the efficiency of the process compared to the prior art through a sequence of different distillation steps.

PRIOR ART

Methyl methacrylate (MMA) is used in large volumes for preparation of polymers and copolymers with other polymerizable compounds. In addition, methyl methacrylate is an important synthesis unit for various specialty esters based on methacrylic acid (MAA), which are prepared, for example, by esterification of MAA with the appropriate alcohols.

MMA is nowadays prepared predominantly proceeding from hydrogen cyanide and acetone via the acetone cyanohydrin (ACH) which forms as a central intermediate. This process has the disadvantage that very large amounts of ammonium sulphate are obtained, and the processing of these is associated with very high costs. Further processes which use a raw material basis other than ACH have been described in the relevant patent literature and have now been implemented on the production scale. In this context, C4-based raw materials such as isobutylene or tert-butanol (TBA) are nowadays also being used as reactants, which are converted over several process stages to the desired methacrylic acid derivatives.

In general, isobutylene or tert-butanol is oxidized here in a first stage to methacrolein, which is subsequently converted to methacrylic acid with oxygen. Methacrylic acid obtained is subsequently converted with methanol to MMA. Further details of this process are given, inter alia, in Ullmann's Encyclopedia of Industrial Chemistry 2012, Wiley-VCH Verlag GmbH & Co, KGaA, Weinheim, Methacrylic Acid and Derivatives, DOI: 10.1002/14356007.a16_441.pub2 and in "Trends and Future of Monomer-MMA Technologies", SUMITOMO KAGAKU 2004-II.

In one modification of this preparation method, rather than from a C4 unit such as isobutylene, it is also possible to proceed from ethylene, which is reacted with synthesis gas first to give propanal and then with formaldehyde to give methacrolein. The methacrolein obtained is oxidized with air in the gas phase over a heterogeneous catalyst to give methacrylic acid and esterified with methanol to give MMA (Ullmann's Encyclopedia of Industrial Chemistry 2012, Wiley-VCH Verlag GmbH & Co, KGaA, Weinheim, Methacrylic Acid and Derivatives, DOI: 10.1002/14356007.a16_441.pub2 "Methacrylic Acid from Ethylene").

In a further process, MMA is obtained by oxidation of isobutylene or TBA with atmospheric oxygen in the gas phase over a heterogeneous catalyst to give methacrolein, and subsequent oxidative esterification reaction of methacrolein using methanol. This process, developed by ASAHI, is described, inter alia, in publications U.S. Pat. No. 5,969,178 and U.S. Pat. No. 7,012,039.

Further problems with all the processes described above are especially also the relatively unsatisfactory yields, high losses in the oxidation steps and hence, in general, associated by-product formation—for example of $CO_2$,—which entail complex process steps for isolation of the product. Thus, all the processes which proceed from isobutylene or equivalent C4-based raw materials such as TBA or methyl tert-butyl ether (MTBE), in gas phase oxidation over a heterogeneous catalyst system, achieve yields below 90%. The relevant literature describes yields below 85% for methacrolein preparation proceeding from isobutylene (for example Table 5 in Ullmann's Encyclopedia, see above).

In addition, patent application CN 101074192 describes a process for preparing MMA, in which methacrolein is initially formed from propanal and formaldehyde at a temperature in the range from 40 to 45° C. and a reaction time in the range from 30 to 100 minutes, and is subsequently oxidized with methanol to MMA. A similar process is also proposed by Yuchao Li et al. "Synthesis of methacrolein by condensation of propionaldehyde with formaldehyde", Advance Materials Research vols. 396-398 (2012), pp. 1094-1097. This publication explicitly advises against working at elevated temperature or an elevated pressure. A disadvantage of this process is the high demand for acid and amine, which are used to catalyse the reaction. This gives rise to large amounts of waste products, since the amine is destroyed in a notable proportion under these conditions. One of the side reactions that deactivates the catalyst is the Eschweiler-Clarke reaction, which leads to the formation of methylated tertiary amine, which is no longer capable of catalysing the Mannich reaction (U.S. Pat. No. 4,408,079, column 2, lines 15 ff.). For example, dimethylamine becomes trimethylamine. To solve these problems, the European patent application with application reference 13002076.1 proposes conducting the Mannich reaction in the first stage at relatively high pressures, and using a noble metal catalyst for the second stage.

A further, very great disadvantage of the direct combination of a Mannich reaction for methacrolein synthesis in a first stage and subsequent oxidative esterification with methanol in a second stage is, however, that methacrylic acid increasingly forms as a by-product in the second stage, as a result of an elevated water content of the crude methacrolein. This methacrylic acid has to be partly or fully neutralized with a relatively large amount of a basic auxiliary, for example NaOH, in order that the MMA target product can be prepared with high selectivities and the catalyst used has long service life. As a result, there is an increase in the amount of waste which arises and in the cost and inconvenience involved in the disposal thereof. The recovery of free MAA or valuable conversion products (MMA) from the mixture thus neutralized again entails the use of an acid and leads to increased waste product formation. This methacrylic acid does not just need to be removed in a costly and inconvenient manner and hence has a yield-reducing effect, but is also harmful to the catalyst used in the second stage. This results in more frequent shutdowns and a higher feedstock consumption overall. JP 2003-192632 describes the connection between the water content and formation of methacrylic acid. However, it is pointed out merely that the water content of methacrolein should be reduced before use in oxidative esterification.

For the less preferred prior art processes, in which, in the first stage, according to publications U.S. Pat. No. 5,969,178 and U.S. Pat. No. 7,012,039, isobutylene or tert-butanol is converted in the gas phase to methacrolein, the problems relating to water content and methacrylic acid formation likewise exist. Therefore, U.S. Pat. No. 5,969,178 and U.S. Pat. No. 7,012,039 teach that the methacrolein from the first stage has to be purified in a very costly and inconvenient, multistage process and especially has to be dewatered in a costly and inconvenient manner, before the product can be transferred into the plant for oxidative esterification.

A further disadvantage of the direct combination of a Mannich reaction and an oxidative esterification with methanol is the raw materials and by-products which are transferred from the first stage into the oxidative esterification of the second stage, and have an adverse effect therein on the space-time yield and/or the catalyst service life and/or the methanol consumption. These raw materials or by-products are, as well as water, which has already been discussed, especially dimeric methacrolein, and formaldehyde and conversion products thereof, especially oligo- and polymers.

Direct oxidative esterification of dimeric methacrolein with methanol, given limited capacity of the catalyst, competes with the same reaction of monomeric methacrolein and hence lowers the space-time yield of the main reaction. This is of great significance especially since the dimeric methacrolein is converted preferentially over the monomeric methacrolein in the oxidative esterification.

The formaldehyde used as reactant in the preparation of methacrolein via a Mannich condensation, and conversion products thereof (especially oligo- and polymers), lead to a multitude of problems in the direct oxidative esterification of methacrolein. Formaldehyde itself has reductive action, which can lead to damage to the catalyst used in the oxidative esterification and hence to shortened catalyst service lives. In addition, formic acid can form under the oxidative conditions, and is likewise harmful to the catalyst. Formaldehyde is known to reversibly form a series of oligo- and polymers (e.g. paraformaldehyde). The hydroxyl end groups of such oligo- and polymers from formaldehyde are reacted with methacrolein in the course of the oxidative esterification, which can lead to polymers that are then stable and insoluble. This is manifested in turbidity of the reaction solution, and solid deposits are observed in the catalyst bed, which can in turn lead to blockage of the apparatus and reduction in the catalyst service life.

Problems

In view of the prior art, the problem addressed by the present invention is therefore that of providing a technically improved process for preparing MMA, which is not afflicted with the disadvantages of conventional processes.

More particularly, the intention is to enable preparation of MMA in a multistage process from propanal and formaldehyde, with increased yield and plant occupation time compared to the prior art.

More particularly, the formation of methacrylic acid during the direct oxidative esterification of methacrolein with methanol to give MMA is to be reduced for this purpose, and hence the consumption of the auxiliary base to adjust the pH.

More particularly, the problem addressed by the present invention was that of reducing the consumption of methanol through the oxidative esterification of by-products of the methacrolein synthesis, for example dimeric methacrolein.

Another problem addressed by the present invention was that of reducing the adverse effects of formaldehyde and conversion products thereof on the direct oxidative esterification of methacrolein.

In addition, the improvement in the process was to be achievable through a very simple and inexpensive modification to existing prior art plants, and was to incur only low maintenance costs in the operation of these plants.

An additional problem addressed by the present invention was that the MMA prepared by the process and a polymethylmethacrylate (PMMA) prepared therefrom were to have particularly low colour.

Further objects not mentioned explicitly will become apparent from the overall context of the description and claims which follow.

Solution

These problems are solved by a novel process for preparing MMA, comprising the following steps:
A) preparing methacrolein from propanal and formaldehyde in the presence of amine salts,
B) isolating crude methacrolein by distillation in a first distillation column and subsequently separating from an aqueous phase,
C) distilling the crude methacrolein obtained from step B) in a second distillation column in the presence of methanol,
D) subsequently oxidatively esterifying the methacrolein obtained from step C) with methanol and oxygen in the presence of a heterogeneous noble metal-containing oxidation catalyst comprising metals and/or metal oxides in a reactor and
E) distilling the product obtained from step D) in a distillation column, and recycling a distillate comprising methacrolein and methanol into the reactor of step D).

Step C) in particular is novel over the prior art. It has surprisingly been possible in accordance with the invention, through an additional distillation between steps B) and D), to reduce the methacrylic acid content in process step D). At the same time, the formation of methacrylic acid in process step D) is reduced. In this way, it has surprisingly additionally been possible to improve the lifetime of the catalyst in step D) and hence the plant occupation time without shutdown for maintenance operations, especially for catalyst renewal. In addition, it has surprisingly been possible to additionally increase the yield of the process compared to the prior art, and to reduce the consumption of auxiliary base, for example sodium hydroxide.

What is especially surprising in this context is that the overall yield of MMA can be increased especially by a distillation in the presence of methanol in step C).

In a particularly preferred embodiment of the invention, the distillation columns which are used in steps C) and E) are the same distillation column. It is thus very surprisingly possible, by means of this embodiment of the invention, to implement the novel process by means of only very minor modifications, especially by means of a modification of the piping, in an existing plant for preparation of MMA from propanal and formaldehyde via a Mannich reaction and a subsequent direct oxidative esterification with methanol.

More preferably, in this embodiment, the methanol in step C) originates from the reactor of step D). In this case, this methanol is passed together with the product from the oxidative esterification in step D) into the distillation column of step E)—and hence of step C). Optionally, further methanol can be added here to this second distillation column, instead of or in addition to the introduction of methanol into the reactor of step D).

More preferably, steps A) to E) of the invention are conducted in a continuous process.

Through the process according to the invention, it is possible in an unforeseeable manner to provide a process for preparing MMA which is not afflicted with the disadvantages of conventional processes. More particularly, it is possible to obtain MMA with a relatively low energy requirement. Furthermore, the process can be conducted in a more environmentally responsible manner compared to the prior art, with smaller amounts of waste obtained and a significant increase in atom economy.

A further great advantage of the process according to the invention is that dimeric methacrolein formed as a by-product in methacrolein synthesis need not be removed at additional cost and inconvenience actually within or directly before process step B), but is instead removed, in the preferred variant of the process according to the invention, in process step C) which was already present in any case. This is because, if this by-product should get into the reactor for process step D), it is converted with consumption of methanol to a corresponding methyl ester by-product. It is thus surprisingly possible through the process according to the invention additionally to reduce the amounts of methanol used.

It has also been found that, surprisingly, the MMA prepared in accordance with the invention and polymers prepared therefrom have a lower colour number than prior art products which have been prepared by means of a combination of Mannich reaction and oxidative esterification.

STEPS C) AND E)

In the distillation in step C), the organic phase from step B), containing the crude methacrolein, is introduced directly into a second distillation column, preferably into the middle part thereof. As already explained, this second distillation column is preferably the same distillation column into which the product from step D) is transferred in step E). In this column, the distillation is effected in the presence of methanol, which is passed directly into the column or, in the preferred embodiment, is fed in from step D) and optionally supplemented with further material fed in.

In this distillation, at least two fractions are obtained. The distillate contains an azeotropic mixture of methanol and methacrolein. This distillate is passed into the reactor of step D). The bottoms from this column from step E) contain predominantly MMA and methanol, water which may still remain in the crude methacrolein after the distillation in step B), and also other higher-boiling constituents, for example dimeric methacrolein. In addition, the bottoms from the column from step C) or E) contain formaldehyde and conversion products thereof. The conversion products of formaldehyde may especially be formaldehyde hydrate (methanediol), and also oligo- and polymers of formaldehyde.

In the preferred embodiment, in which steps C) and E) are conducted in the same column, it is optionally possible to pass a substream of the crude methacrolein from step B), especially from the phase separator, directly into the reactor of step D) or into the feed of the azeotropic mixture of methacrolein and methanol from the column from step E) into the reactor of step D). Such an embodiment is especially suitable for achieving a higher methacrolein concentration in step D). In this way, small amounts of water and dimeric methacrolein are additionally passed into the reactor. Nevertheless, even with such an embodiment, the formation of methacrylic acid and the consumption of methanol are reduced. In general, the ratio of the amount of methacrolein in the stream from step B) to the sum of the amounts of methacrolein from steps B) and E) is less than 0.7, preferably less than 0.5, more preferably less than 0.3 and most preferably less than 0.1.

In the embodiment with different columns for steps C) and E), it is likewise possible to conduct a substream from process step B) directly into the reactor of step D).

Preferably, a third fraction is also withdrawn from the distillation column in step C) or E). This third fraction is a low boiler stream which is removed at the top of column C) or E) and disposed of. In process step E), this low boiler stream contains methyl formate, for example. In addition, the low boiler stream from column C may contain small amounts of methylal, the dimethyl acetal of formaldehyde. For separation of the first fraction, referred to as distillate in the previous section, this first fraction is preferably withdrawn in the uppermost third of the column as a sidestream, but not at the top of the column, while the low boiler stream is removed directly in gaseous form or in condensed form at the top of the column and sent, for example, to an incineration.

The column bottoms from process step E), comprising MMA and methanol in particular, in a first alternative, are fed into an extraction. In this extraction apparatus, while feeding in water, the bottoms stream is separated into an organic phase and an aqueous phase. The aqueous phase is removed and passed, for example, to incineration in a thermal oxidizer or else into another kind of wastewater processing operation.

A further, additional advantage of the process according to the invention is that, in process step C) or E), dimeric methacrolein which is unavoidably formed in process step A), and which is the product of a Diels-Alder reaction of two methacrolein molecules, is removed before it is passed into the reaction space for the oxidative esterification in process step D). In process step D), this dimeric methacrolein, as in the processes known from the prior art, would be converted to a corresponding methyl ester. Through the process according to the invention, it is possible, inter alia, to reduce the methanol consumption of the overall process, since dimeric methacrolein is esterified to a smaller extent, if at all, in process step D). In addition, the dimeric methacrolein, given a limited catalyst capacity, would compete with the oxidative esterification of the monomeric methacrolein and hence additionally lower the space-time yield. This is of great significance especially since the dimeric methacrolein is converted preferentially over the monomeric methacrolein in the oxidative esterification.

In addition, in process step D), the dimeric methacrolein would also form corresponding acid. Analogously to methacrylic acid, this acid has adverse effects on the catalyst service life and would therefore have to be neutralized with an auxiliary base as described for methacrylic acid. In addition, this acid or the salt thereof remains in the column bottoms of process step E) and can lead to deposits later in the process, for example in the distillation columns. The process according to the invention additionally avoids this problem.

The compound referred to in this application as dimeric methacrolein or synonymously as dimethacrolein is 2,5-dimethyl-3,4-dihydro-2H-pyran-2-carbaldehyde.

The methyl ester of dimethacrolein, which is barely formed, if at all, in accordance with the invention, is a major problem in prior art processes. Because of formation of azeotropes and poor water solubility, this methyl ester is entrained into the columns for MMA purification. Under the conditions that exist in these columns, there is a partial retro-Diels-Alder reaction which forms, as well as an equivalent of MMA, also an equivalent of methacrolein, which is now disruptive. This polymerization-active methacrolein can enter into side reactions therein, which lead in turn to formation of oligomeric constituents and a reduced purity of the end product. The latter can lead inter alia to an elevated colour number in the end product. Furthermore, methacrolein, even in small amounts in the end product, is problematic in relation to toxicity and the general product properties.

It is a further advantage of the present invention that, in process step C) or E), formaldehyde residues from process steps A) and B) are also removed and hence are not transferred into process step D). The removal is effected in the bottom of the respective column in the form of methanediol and/or in the form of oligo- and polymers of formaldehyde. Formaldehyde would lead to a multitude of problems in process step D).

Formaldehyde itself has reductive action, which can lead to damage to the catalyst used in the oxidative esterification and hence to shortened catalyst service lives. In addition, formic acid can form under the oxidative conditions, and is likewise harmful to the catalyst. Formaldehyde is known to reversibly form a series of oligo- and polymers (paraformaldehyde). The hydroxyl end groups of such oligo- and polymers from formaldehyde are converted by methacrolein in the course of the oxidative esterification, which leads to polymers that are then stable and usually insoluble. These polymers can in turn lead to blockage of the apparatus and reduction in the catalyst service life.

In one embodiment, in which the columns of steps C) and E) are not identical, the bottoms from the column from step C) are preferably disposed of as wastewater. However, these bottoms can alternatively also be passed fully or partly into the column from step B) or into the reactor from step A).

The operation of the column of step E), into which only the reaction mixture from step D) and not the crude methacrolein from step B) is fed, is described, for example, in JP2006-225401. It is also stated here that it is advantageous to feed the reaction mixture into the middle of the column. Following this teaching, it is correspondingly preferable in accordance with the invention that both the reaction mixture of step D) and, in the preferred embodiment, the crude methacrolein of step B) are passed into the middle of the column of step E). In the alternative embodiment of two separate columns for steps C) and E), feeding into the middle of each of the columns is correspondingly preferable.

In a second alternative, the bottoms from the distillation column from process step E), irrespective of the rest of the embodiment of the invention, are transferred into a phase separator. The MMA-containing bottoms introduced are separated therein into an organic phase and an aqueous phase. This alternative is an option particularly in the case of a relatively high water content of the bottoms.

The organic phase obtained from these alternatives, for further workup of the MMA, can be run into a further one to four series-connected distillation columns. In this case, for example, the MMA-containing phase can alternately first be obtained as distillate of the respective column and then as bottoms of the column. In this way, both higher-boiling and low-boiling impurities can be removed virtually completely from the MMA.

Preferably in accordance with the invention, the stream from step C) or E) passed into the reactor of step D)—referred to previously as distillate of the second distillation column—includes, as well as methanol and methacrolein, an amount of water smaller than the amount of water in the crude methacrolein from step B).

More preferably, the sidestream passed out of step C) or E) to step D) has a water content less than 0.5% by weight, more preferably less than 0.1% by weight and especially preferably less than 500 ppm.

In the present invention, there is no particular restriction with regard to the design of the distillation columns used. It is possible to use any desired types of conventional distillation columns, tray columns or packed columns.

Since, however, crude methacrolein which is introduced into the distillation tower in step C) or E) is a readily polymerizable compound, it is preferable to use a still having a structure in which blockage with polymerization products does not occur and/or the polymerization products can be removed easily. Specific examples of distillation towers include tray columns equipped with a sieve tray, cascade tray, turbogrid tray, ripple tray or the like, and packed columns packed with packing materials in a regular fashion (for example Mellapak from Sulzer) or in an irregular fashion (for example Raschig Superring from Raschig).

In the process according to the invention, the suitable distillation temperature in the distillation tower varies as a function of distillation pressure, the composition of the liquid in the distillation tower, the number of trays in the distillation tower and the like. In order, however, to restrict the formation of the aforementioned polymerization products and the formation of high-boiling compounds, which constitute a yield loss of methacrolein or MMA, to a minimum, it is preferable that the distillation temperature is as low as possible. However, if the distillation temperature selected is too low, disadvantages can occur. One example of these is that the distillation pressure selected also has to be low. As a result of this, it may be necessary to use the distillation tower in a disadvantageous size. In addition, the use of a coolant for condensation of the gas phase in the uppermost part of the distillation tower may be required. The distillation temperature or the temperature of the liquid in the column is preferably in the range from 20 to 100° C., more preferably from 40 to 85° C. The distillation pressure arises from this temperature.

Unless explicitly stated otherwise, all details in the present text apply both to embodiments in which there are separate distillation towers in steps C) and E) and to embodiments in which the distillation towers of steps C) and E) are the same apparatus.

In addition, it should be pointed out that the terms "distillation tower", "distillation column" and "column" are used synonymously in this text.

STEPS A) AND B)

The process according to the invention comprises, in process step A), the preparation of methacrolein by reaction of propanal with formaldehyde via an aldol or Mannich condensation. The formaldehyde can be used here, for example, in the form of formalin. The processes suitable for this purpose are known to those skilled in the art and are the subject of corresponding review articles, for example in Ullmann's Encyclopedia of Industrial Chemistry 2012, Wiley-VCH Verlag GmbH & Co. KGaA, Weinheim, Acrolein and Methacrolein, DOI: 10.1002/14356007.a01_149.pub2. More particularly, reference should also be made to the particularly preferred version of this step A), as described in the European patent application having the reference number 13002076.1.

Preferably, the conversion in process step A) is conducted in the presence of 0.1 to 20 mol % of organic base, preferably a secondary amine, and 0.1 to 20 mol % of acid, based in each case on the propanal, at a temperature of 100 to 300° C. and at a pressure of 5 to 100 bar.

In the preparation of methacrolein from propanal and formaldehyde, the reaction mixture in step B) is fed to a column and stripped therein, preferably with steam. The methacrolein leaves the column overhead together with water. The mixture is condensed and preferably separated by means of a phase separator, especially a phase separation vessel, into an upper phase and a lower phase. The upper phase contains the methacrolein, residues of formaldehyde, propanal and the dimethacrolein by-product, and is passed onward into the distillation in step C) and subsequently to the oxidative esterification in step D) to give MMA. The lower phase consists principally of water. It can preferably be recycled at least partly back into the column for removal of the methacrolein still dissolved therein.

In general, a condenser is also present between the distillation column and the phase separator.

The water content of the crude methacrolein from step B) can vary as a function of temperature. Preferably, the reaction mixture obtained after the reaction of formaldehyde with propanal is accordingly cooled to a temperature at which the water content in the methacrolein phase is established. Preferably, the temperature in the phase separator can be set between 0 and 50° C., preferably 5 to 30° C. and more preferably 10 to 25° C.

The aqueous catalyst solution can be drawn off at the bottom of the column together with the water formed in the reaction and the water from the formaldehyde solution used. For the further processing, if very little amine and/or acid is used and therefore it is not worth recycling the catalyst, the bottoms liquid can be discarded.

In the case of greater amine and/or acid concentrations in the bottoms output, however, it is also possible to partly remove water by distillation and to recycle the remaining catalyst solution back into the reactor. It is also possible to divide the bottoms output into two substreams such that one substream carries precisely the amount of water which has been formed in the reaction and introduced with the starting materials. This substream is then discharged and the remaining proportion is recycled into the reactor. Aqueous formaldehyde and propanal can also be preheated separately and fed to the reactor. It is also possible to isolate the water from the bottoms output by means of one or more membrane separation stages.

STEP D)

According to the invention, the methacrolein obtained in step A) and worked up in steps B) and C) is converted to MMA in a direct oxidative esterification reaction in step D). In the context of the present invention, a direct oxidative esterification reaction is understood to mean a process in which methacrolein is converted to MMA directly, i.e. without the formation of any great amounts of methacrylic acid, in the presence of methanol and an oxidizing agent, preferably oxygen. More particularly, reference should also be made to the particularly preferred version of this step D), as described in the European patent application having the reference number 13002076.1.

In the oxidative esterification reaction in step D), preference is given to using heterogeneous oxidation catalysts comprising one or more ultrafinely distributed metals having an average particle size of <20 nm. These metals are preferably gold, palladium, ruthenium, rhodium or silver, or mixtures thereof. Further preferably, the reaction in step D) is conducted at a pressure of 1 to 100 bar, preferably of 2 to 50 bar, in the liquid phase. Preferably, the reaction temperature in step D) is within a range from 10 to 200° C.

Preferably, the oxidative esterification reaction in step D) is effected with a molar ratio of methanol to methacrolein in the range from 1:1 to 50:1.

According to the invention, not more than 2% by weight, preferably not more than 1% by weight and more preferably not more than 0.5% by weight of free methacrylic acid forms from methacrolein in the oxidative esterification reaction in step D), and this is partly or fully neutralized with a basic auxiliary, for example sodium hydroxide.

Preferably, the water content of the reaction mixture present in the steady state for oxidative esterification in step D) is not more than 5.0% by weight. The majority of this water is that which is formed in the oxidative esterification in step D).

The oxidative esterification under the aforementioned conditions affords a reaction mixture containing MMA as the main reaction product. In addition to MMA, the reaction mixture obtained also contains unconverted methacrolein and unconverted methanol and water formed in the reaction and possibly the amounts of methacrylic acid mentioned as by-products. The reaction mixture may also contain other components and by-products including very small amounts of dimeric methacrolein, the methyl ester thereof and others.

Because of the polymerizability of these constituents, it is preferable that one or more polymerization inhibitors are added to the process, especially to the distillation tower in process step C) and/or E). Polymerization inhibitors, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidine 1-oxyl, p-phenylenediamine, methylene blue or sterically hindered phenols, are widely known in the specialist field. These compounds can be used individually or in the form of mixtures and are generally commercially available. The effect of the stabilizers is usually that they work as free-radical scavengers for the free radicals which occur in the polymerization. For further details, reference is made to the standard specialist literature, especially to the Römpp-Lexikon Chemie [Römpp's Chemistry Lexicon]; editors: J. Falbe, M. Regitz; Stuttgart, N.Y.; 10th edition (1996); under the heading "Antioxidantien" [Antioxidants] and the references cited there.

LIST OF REFERENCE NUMERALS

FIG. 1 shows, in schematic form, the most important plant constituents for performance of the process according to the invention in the embodiment with separate distillation columns for steps C) and E).

(1) reactor for step A)
(2) reactor for step D)
(3) distillation column for step B)
(4) condenser for distillation column (3)
(5) phase separator from step B)
(6) distillation column from step C)
(7) distillation column from step E)
(8) separation of aqueous and organic phases (optional)
(9) removal of high-boiling constituents (optional)
(10) removal of low-boiling constituents
(11) methanol feed; as desired, into distillation column (6) and/or into reactor (2); optionally also feed for a stabilizer solution
(12) air or oxygen feed

(13) feed for further process substances, for example auxiliary base or the like
(14) wastewater, optionally all or some for recycling into (1), (3) or (5)
(15) optional offgas
(16) offgas
(17) offgas
(18) wastewater
(19) high-boiling waste
(20) prepurified MMA for optional further purification, for example by further distillation
(21) feed for the distillate from (6) (stage C)), containing a mixture of methacrolein and methanol, into (2)
(22) feed for the distillate from (7) (stage E)), containing a mixture of methacrolein and methanol, into (2)
(23) feed of the reaction mixture from (2) (stage D)) into (7) (for stage E))
(24) passage of the MMA-containing bottoms from stage E) (7) into the separation stage (8)
(25) passage of the organic phase from (8) into distillation column (9)
(26) passage of the distillate from (9) into distillation column (10)
(27) passage of the vapour from (3) into condenser (4)
(28) passage of the condensate from (4) into phase separator (5)
(29) wastewater, optionally all or some for recycling into (1)
(30) optional fee of water or aqueous acid into (8)
(31) feed of the organic phase from the phase separator (5) from step B) into the distillation column (6) of step C)

FIG. 2 shows, in schematic form, the most important plant constituents for performance of the process according to the invention in the preferred embodiment with a common distillation column for steps C) and E).

(1) reactor for step A)
(2) reactor for step D)
(3) distillation column for step B)
(4) condenser for distillation column (3)
(5) phase separator from step B)
(8) separation of aqueous and organic phases (optional)
(9) removal of high-boiling constituents (optional)
(10) removal of low-boiling constituents
(12) air or oxygen feed
(13) feed for further process substances, for example auxiliary base or the like
(16) offgas
(17) offgas
(18) wastewater
(19) high-boiling waste
(20) prepurified MMA for optional further purification, for example by further distillation
(22) feed for the distillate from (33) (stage E)), containing a mixture of methacrolein and methanol, into (2)
(23) feed of the reaction mixture from (2) (stage D)) into (33) (for stage E))
(24) passage of the MMA-containing bottoms from stage E) (33) into the separation stage (8)
(25) passage of the organic phase from (8) into distillation column (9)
(26) passage of the distillate from (9) into distillation column (10)
(27) passage of the vapour from (3) into condenser (4)
(28) passage of the condensate from (4) into phase separator (5)
(29) wastewater, optionally all or some for recycling into (1)
(30) optional feed of water or aqueous acid into (8)
(32) feed of the organic phase from the phase separator (5) from step B) into the distillation column (33) of step C)
(33) distillation column for steps C) and E)
(34) methanol feed; as desired, into distillation column (33) and/or into reactor (2); optionally also feed for a stabilizer solution
(35) optional line for substream from phase separator (5) into reactor (2)

With regard to the drawings, it should be noted that further components known to those skilled in the art may additionally be present in the plant for performance of the process according to the invention. For example, each of the columns detailed generally has a condenser. In the drawings, a corresponding condenser (4) is shown only for the first column (3) for performance of process step B).

It should also be noted that not every preferred embodiment is included in the drawings. For example, it is also possible for the embodiment according to FIG. 1, with separate columns (6) and (7) for process steps C) and E), to have an optional line (35) for the substream from phase separator (5) into reactor (2), even though this line (35) is not included in FIG. 1.

The position of the feeds does not indicate the real location thereof, but merely indicates the apparatus into which the feed is conducted.

The invention claimed is:

1. A process for preparing methyl methacrylate, comprising the steps of:
   A) preparing methacrolein from propanal and formaldehyde in the presence of amine salts;
   B) isolating liquid crude methacrolein by distillation in a first distillation column and subsequently separating from an aqueous phase;
   C) distilling the crude methacrolein obtained from step B) in a second distillation column in the presence of methanol;
   D) subsequently oxidatively esterifying the methacrolein obtained from step C) with methanol and oxygen in the presence of a heterogeneous noble metal-containing oxidation catalyst comprising metals and/or metal oxides in a reactor; and
   E) distilling the product obtained from step D) in a distillation column, and recycling a distillate comprising methacrolein and methanol into the reactor of step D).

2. The process according to claim 1, wherein the distillation columns of steps C) and E) are the same distillation column.

3. The process according to claim 2, wherein a mixture of methanol and methacrolein from the distillation column of step E) is recycled into the reactor of step D), and further methanol is optionally added to the second distillation column in step E).

4. The process of claim 2, wherein a substream of the crude methacrolein from step B) is passed into the reactor of step D), and in that the ratio of this substream to the stream from the distillation column of step E) into the reactor of step D) is between 1:2 and 1:20.

5. The process of claim 1, wherein in process step C) or B), dimethacrolein is removed together with the column bottoms and an amount of dimethacrolein less than the amount in the stream which is introduced from process step B) into process step C) is introduced into process step D).

6. The process of claim 1, wherein the heterogeneous oxidation catalyst used for the oxidative esterification reaction in step D) comprises one or more ultrafinely divided metals having an average particle size of <20 nm, selected from the group consisting of gold, palladium, ruthenium, rhodium and silver, and in that the reaction in step D) is conducted at a pressure of 1 to 100 bar in the liquid phase.

7. The process of claim 1, wherein the conversion in step D) is conducted at a pressure in the range from 2 to 50 bar and at a temperature in the range from 10 to 200° C. in the liquid phase.

8. The process of claim 1, wherein in the distillation column of step E), a low boiler stream comprising methyl formate is removed overhead and disposed of.

9. The process of claim 1, wherein the oxidative esterification reaction in step D) is effected with a molar ratio of methanol to methacrolein in the range from 1:1 to 50:1.

10. The process of claim 1, wherein steps A) to E) are conducted in a continuous process.

11. The process of claim 1, wherein the bottoms from the second distillation column of step E) are transferred into an extraction in which water is used to separate the stream into an organic phase and an aqueous phase.

12. The process of claim 1, wherein the bottoms from the second distillation column of step E) are transferred into a phase separator and separated therein into an organic phase and an aqueous phase.

13. The process of claim 11, wherein the respective organic phase is purified further in at least one further distillation step.

14. The process of claim 1 wherein the stream from step C) or E), comprising methanol and methacrolein, passed into the reactor of step D) includes an amount of water less than the amount of water in the crude methacrolein from step B).

15. The process of claim 1, wherein the separation from the aqueous phase after step B) is effected in a phase separator.

16. The process of claim 1, wherein the conversion in process step A) is conducted in the presence of 0.1 to 20 mol % of organic base, and 0.1 to 20 mol % of acid, based in each case on the propanal, at a temperature of 100 to 300° C. and at a pressure of 5 to 100 bar.

* * * * *